United States Patent
Wang et al.

(10) Patent No.: US 11,836,644 B2
(45) Date of Patent: Dec. 5, 2023

(54) ABNORMAL AIR POLLUTION EMISSION PREDICTION

(71) Applicant: International Business Machines Corporation, Armonk, NY (US)

(72) Inventors: Lingyun Wang, Beijing (CN); Junmei Qu, Beijing (CN); Xi Xia, Beijing (CN); Xin Xin Bai, Beijing (CN); Jin Yan Shao, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 418 days.

(21) Appl. No.: 16/532,543

(22) Filed: Aug. 6, 2019

(65) Prior Publication Data

US 2021/0042648 A1     Feb. 11, 2021

(51) Int. Cl.
G06N 5/04     (2023.01)
G01W 1/10     (2006.01)
G16Z 99/00    (2019.01)
G01N 33/00    (2006.01)
G06N 5/048    (2023.01)

(52) U.S. Cl.
CPC .............. *G06N 5/048* (2013.01); *G01W 1/10* (2013.01); *G16Z 99/00* (2019.02); *G01N 33/0004* (2013.01)

(58) Field of Classification Search
CPC ......... G06N 5/048; G16Z 99/00; G01W 1/10; G01N 33/0004
See application file for complete search history.

(56) References Cited

U.S. PATENT DOCUMENTS

| | | | |
|---|---|---|---|
| 5,604,299 A | 2/1997 | Cobb | |
| 2009/0309744 A1* | 12/2009 | Fu | G08B 27/006 340/632 |
| 2016/0125307 A1* | 5/2016 | Zheng | G06N 20/00 706/12 |
| 2016/0370339 A1* | 12/2016 | Liu | G01N 33/0075 |
| 2017/0184561 A1* | 6/2017 | Bai | G01N 33/0062 |
| 2017/0316328 A1* | 11/2017 | Dong | G06Q 10/063 |
| 2018/0082199 A1* | 3/2018 | Liu | G06K 9/00 |
| 2018/0188050 A1* | 7/2018 | Duan | G08G 1/0141 |

FOREIGN PATENT DOCUMENTS

| | | | |
|---|---|---|---|
| CN | 104881546 | * | 9/2015 |
| CN | 107436343 A | | 12/2017 |
| CN | 106153510 | * | 6/2019 |

* cited by examiner

*Primary Examiner* — Mohamed Charioui
*Assistant Examiner* — Lynda Dinh
(74) *Attorney, Agent, or Firm* — Patterson + Sheridan, LLP

(57) ABSTRACT

A method, a device and a computer program product for abnormal air pollution emission prediction are proposed. In the method, a first set of features characterizing air condition in a zone is obtained. Whether the zone is subject to abnormal air pollution emission in a future first time period is determined based on the first set of features and using a first prediction classifier. In response to determining that the zone is subject to abnormal air pollution emission in the first time period, a second set of features characterizing air condition in the zone is obtained. A future second time period in which the zone is subject to abnormal air pollution emission is determined based on the second set of features and using a second prediction classifier. The second time period is included in the first time period. In this way, the abnormal air pollution emission in the zone can be accurately and efficiently predicted.

20 Claims, 6 Drawing Sheets

| TARGET AREA | NUMBER OF ZONES BEING PREDICTED TO BE SUBJECT TO ABNORMAL AIR POLLUTION PREDICTION | ACCURACY |
|---|---|---|
| BAODING | 260 | 72.7% |
| TANGSHAN | 189 | 78.6% |
| LANGFANG | 180 | 72.1% |
| HENGSHUI | 133 | 88.2% |
| XINGTAI | 133 | 100.0% |

FIG. 7

ABNORMAL AIR POLLUTION EMISSION PREDICTION

BACKGROUND

The present invention relates to information processing, and more specifically, to a method, a device and a computer program product for abnormal air pollution emission prediction.

Nowadays, air pollution is of great concern. In order to reduce the air pollution, air pollutant emission needs to be monitored and predicted. A known approach for monitoring the air pollutant emission is grid monitoring. However, in the grid monitoring, a grid with a high level of abnormal air pollution emission cannot be accurately predicted in time, and a huge amount of time and resource needs to be devoted in dealing with the abnormal air pollution emission prediction in the grid monitoring.

SUMMARY

According to one embodiment of the present invention, there is provided a method for abnormal air pollution emission prediction. In the method, a first set of features characterizing air condition in a zone is obtained. Whether the zone is subject to abnormal air pollution emission in a future first time period is determined based on the first set of features and using a first prediction classifier. In response to determining that the zone is subject to abnormal air pollution emission in the first time period, a second set of features characterizing air condition in the zone is obtained. A future second time period in which the zone is subject to abnormal air pollution emission is determined based on the second set of features and using a second prediction classifier. The second time period is included in the first time period.

According to another embodiment of the present invention, there is provided a device for abnormal air pollution emission prediction. The device comprises a processing unit and a memory coupled to the processing unit and storing instructions thereon. The instructions, when executed by the processing unit, performing acts including: obtaining a first set of features characterizing air condition in a zone; determining, based on the first set of features and using a first prediction classifier, whether the zone is subject to abnormal air pollution emission in a future first time period; in response to determining that the zone is subject to abnormal air pollution emission in the first time period, obtaining a second set of features characterizing air condition in the zone; and determining, based on the second set of features and using a second prediction classifier, a future second time period in which the zone is subject to abnormal air pollution emission, the second time period being included in the first time period.

According to yet another embodiment of the present invention, there is provided a computer program product being tangibly stored on a non-transient machine-readable medium and comprising machine-executable instructions. The instructions, when executed on a device, causing the device to perform acts including: obtaining a first set of features characterizing air condition in a zone; determining, based on the first set of features and using a first prediction classifier, whether the zone is subject to abnormal air pollution emission in a future first time period; in response to determining that the zone is subject to abnormal air pollution emission in the first time period, obtaining a second set of features characterizing air condition in the zone; and determining, based on the second set of features and using a second prediction classifier, a future second time period in which the zone is subject to abnormal air pollution emission, the second time period being included in the first time period.

BRIEF DESCRIPTION OF THE SEVERAL VIEWS OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

FIG. 7 shows a schematic diagram of an example abnormal air pollution emission prediction result according to an embodiment of the present invention.

DETAILED DESCRIPTION

Figure 1:
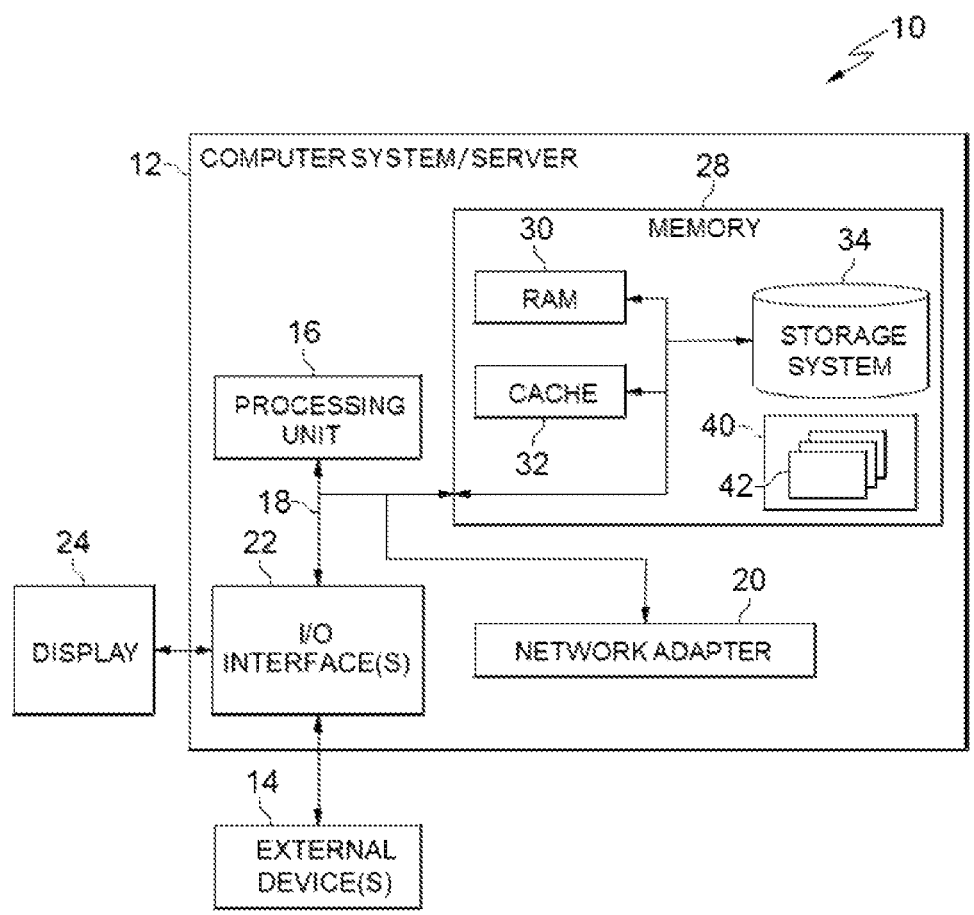
FIG. 1 depicts a cloud computing node according to an embodiment of the present invention.

Some embodiments will be described in more detail with reference to the accompanying drawings, in which the embodiments of the present disclosure have been illustrated. However, the present disclosure can be implemented in various manners, and thus should not be construed to be limited to the embodiments disclosed herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12 or a portable electronic device such as a communication device, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/ non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
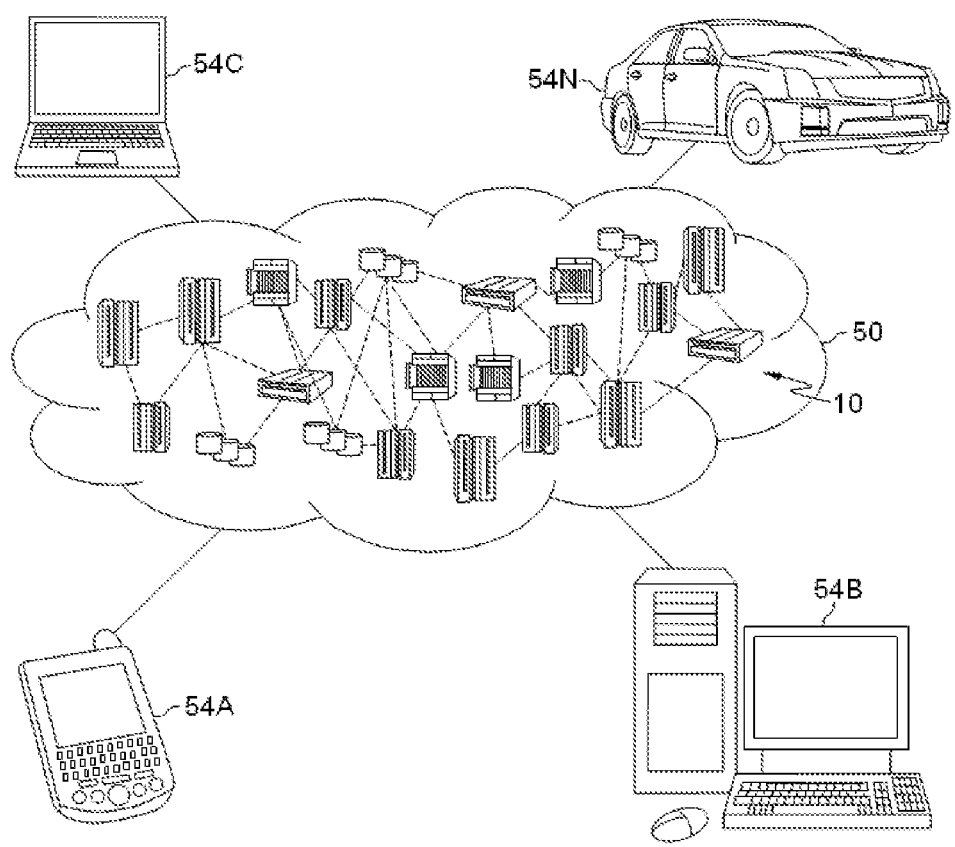
FIG. 2 depicts a cloud computing environment according to an embodiment of the present invention.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
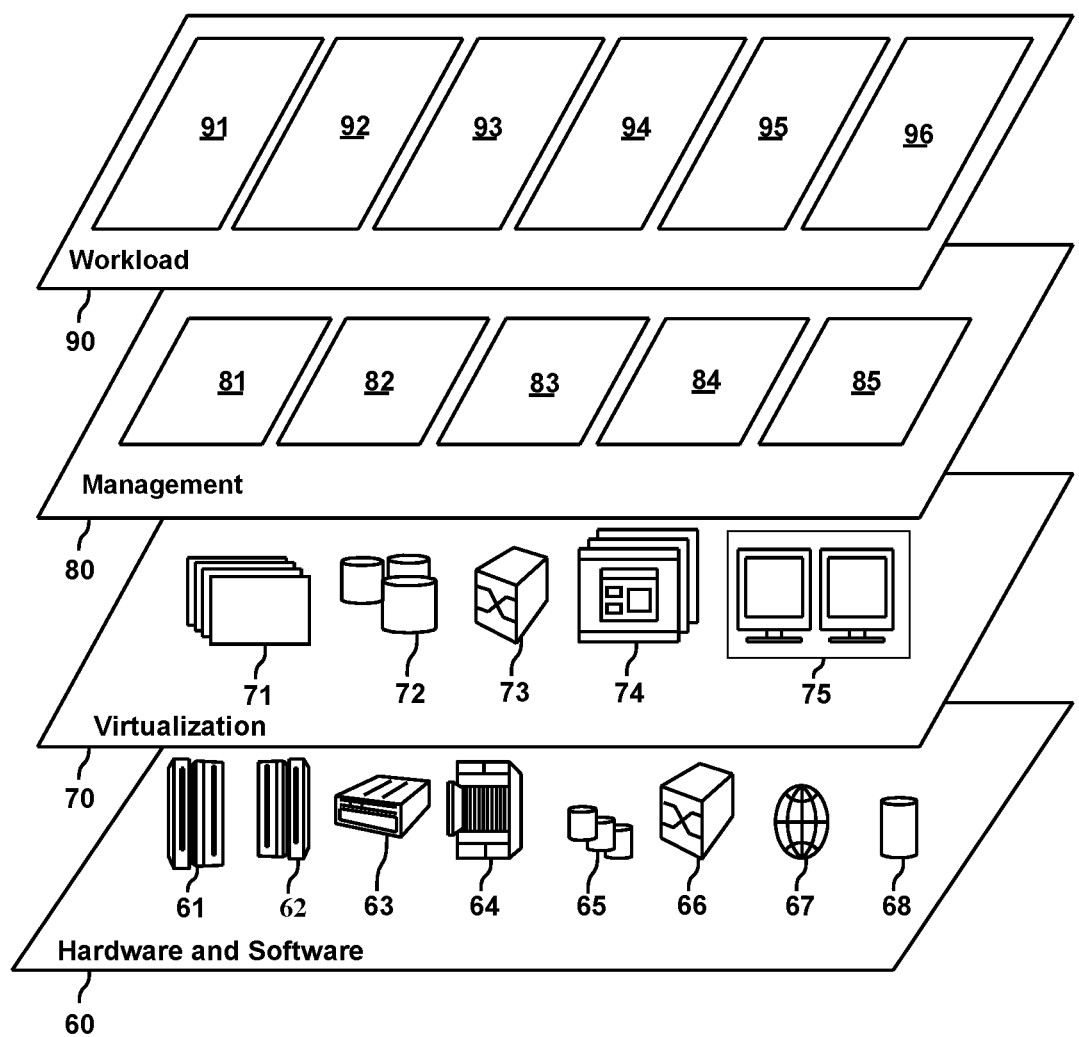
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and abnormal air pollution emission predicting 96.

As discussed above, the grid monitoring for the abnormal air pollution emission suffers from inaccuracy and high cost of time and resource. For example, manual inspection of the air pollutant emission for an entity, such as an enterprise, costs a huge amount of time and manpower and is not performed in time. In addition, comparing the instantaneous air pollutant emission of an entity with that of its surroundings in real time may cause a false alarm for an emission behavior or miss the real emission behavior.

In order to at least partially solve one or more of the above problems and other potential problems, example embodiments of the present disclosure propose a solution for abnormal air pollution emission prediction.

Generally speaking, according to embodiments of the present disclosure, the target area for abnormal air pollution emission is divided into a plurality of zones or grids, such that a zone or grid can be used as a unit for the abnormal air pollution emission prediction. The abnormal air pollution emission means a potential pollution source in a zone abnormally emits air pollutant into the environment. For example, a factory in a zone emits a significantly high amount of air pollutant into the air.

Then, one or more zones including a potential pollution source are selected from the plurality of zones. For each selected zone, it is determined whether the selected zone is subject to abnormal air pollution emission in a future time period (referred to as "first time period") based on a set of features (referred to as "first set of features") characterizing air condition in the zone. The first set of features covers various factors related to the abnormal air pollution emission, such that the occurrence of the abnormal air pollution emission in the selected zone can be precisely predicted. These factors may include the historical air pollution information, for example, historical cumulative concentration information, historical abnormal air pollution emission information etc. In addition, these factors may also involve other historical air condition, for example, wind speed, wind direction, temperature, etc.

If the selected zone is determined to be subject to abnormal air pollution emission in the first time period, a more specific time period (referred to as "second time period") during which the abnormal air pollution emission occurs in this zone can be further determined based on another set of features (referred to as "second set of features") characterizing air condition in the zone. Since it has been already determined that the selected zone will be subject to abnormal air pollution emission, the second set of features mainly considers the historical air pollution information, such that the most likely time period that the abnormal air pollution emission occurs can be predicted.

By way of example, it is possible to first determine whether a zone including a potential pollution source will be subject to abnormal air pollution emission in the future, for example tomorrow. If the zone will be subject to abnormal air pollution emission tomorrow, it is then determined when the zone is most likely to be subject to abnormal air pollution emission tomorrow. For example, it can be determined that the zone is most likely to be subject to abnormal air pollution emission at 1 am-2 am. Such prediction can be used for various purposes. For example, the prediction that the zone will be subject to abnormal air pollution emission at 1 am-2 am tomorrow can be provided to regulators for investigating the abnormal air pollution emission condition in this zone at 1 am-2 am tomorrow. In addition, such prediction can also be provided to the potential pollution sources, for example, to help them control and improve their emission behavior. As another example, such prediction can also be used by other users, such as alarming the users to avoid entering into the polluted zones.

In this way, abnormal air pollution emission condition for the zone can be predicted accurately in time, and time and resource cost for the abnormal air pollution emission prediction can be reduced.

Figure 4:
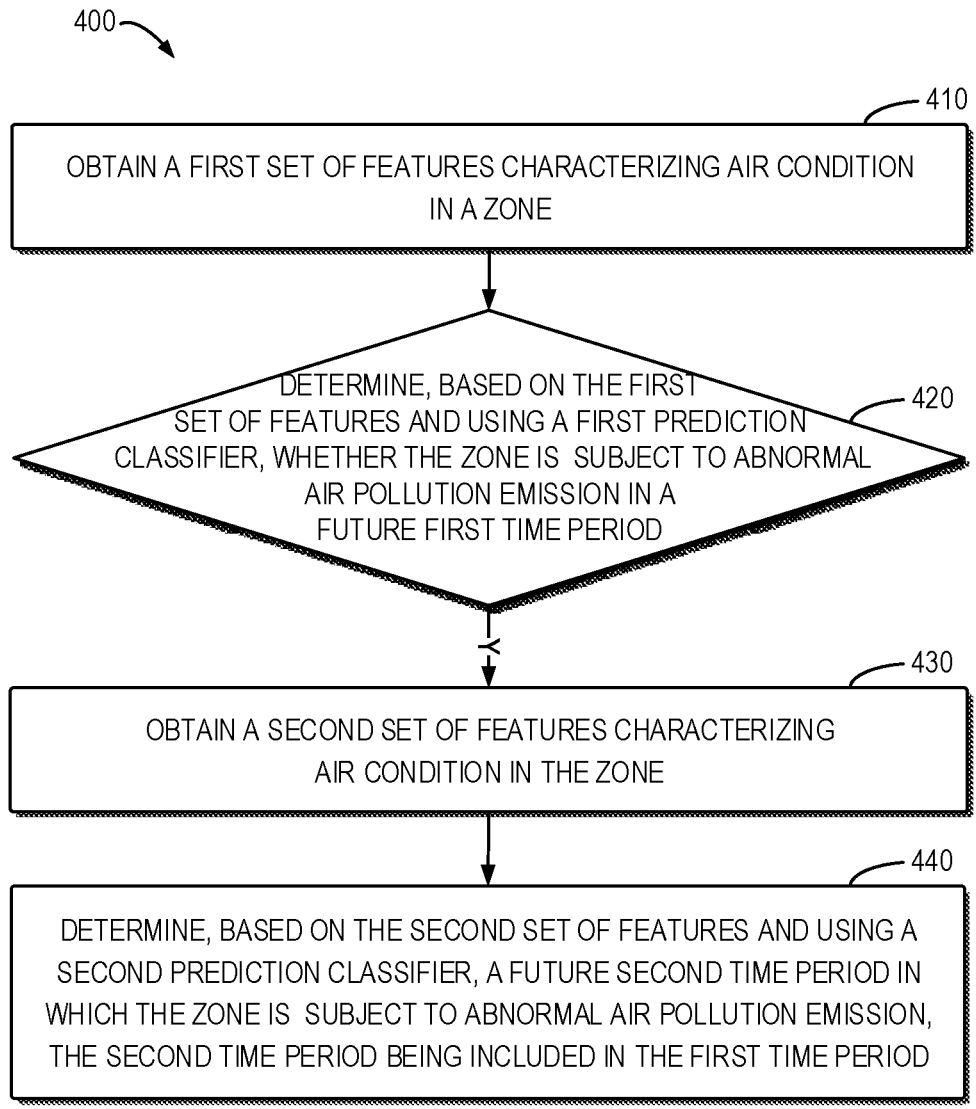
FIG. 4 shows a flow chart of an example method for abnormal air pollution emission prediction according to an embodiment of the present invention.

Now some example embodiments will be described with reference to FIGS. 4-7. FIG. 4 shows a flow chart of an example method 400 for abnormal air pollution emission prediction according to an embodiment of the present invention. The method 400 may be at least in part implemented by the computer system/server 12, or other suitable systems.

At 410, the computer system/server 12 obtains a first set of features characterizing air condition in a zone. As discussed above, in order to predict abnormal air pollution emission condition for an area, such as a city, the area can be divided into a plurality of zones or grids, so as to improve the accuracy of the prediction. In this case, a zone or grid can be used as a unit for the abnormal air pollution emission prediction. The zone or grid may have a predetermined size and shape. For example, the zone or grid may represent a square-shaped zone, which is 500-meter in width and 500-meter in length, in the city.

In some embodiments, the computer system/server 12 may obtain the first set of features from the system memory 28. Alternatively, the first set of features may be obtained from any storage or database storing the first set of features.

The first set of features may include any feature that characterizes air condition in a zone. In some embodiments, these features may be historical information sampled in a past time period (referred to as "third time period"), such as the past 24 hours. For example, these features may be historical cumulative concentration information characterizing air pollutant concentration accumulated in the zone in the third time period, historical wind speed in the zone in the third time period, historical wind direction in the zone in the third time period, or historical temperature in the zone in the third time period.

In addition to the historical information sampled in the third time period, these features may also include other historical information. For example, these features may be a number of times the zone being previously determined to be subject to abnormal air pollution emission in a past fourth time period, such as the past month, whether the zone was determined to be subject to abnormal air pollution emission in a fifth time period, such as the past week, or time since the zone was last determined to be subject to abnormal air pollution emission. It is to be understood that, these past time periods, i.e. the third, fourth and fifth time periods, are determined independently according to the abnormal air pollution emission prediction policy.

Figure 5:
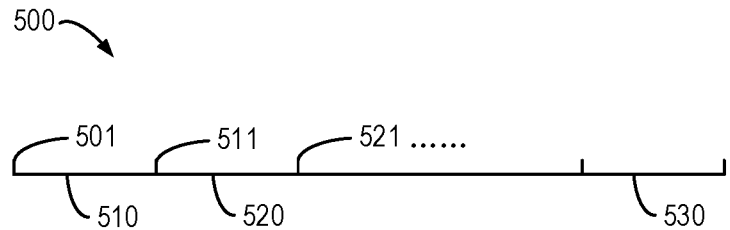
FIG. 5 shows a schematic diagram of an example time period according to an embodiment of the present invention.
Figure 6:
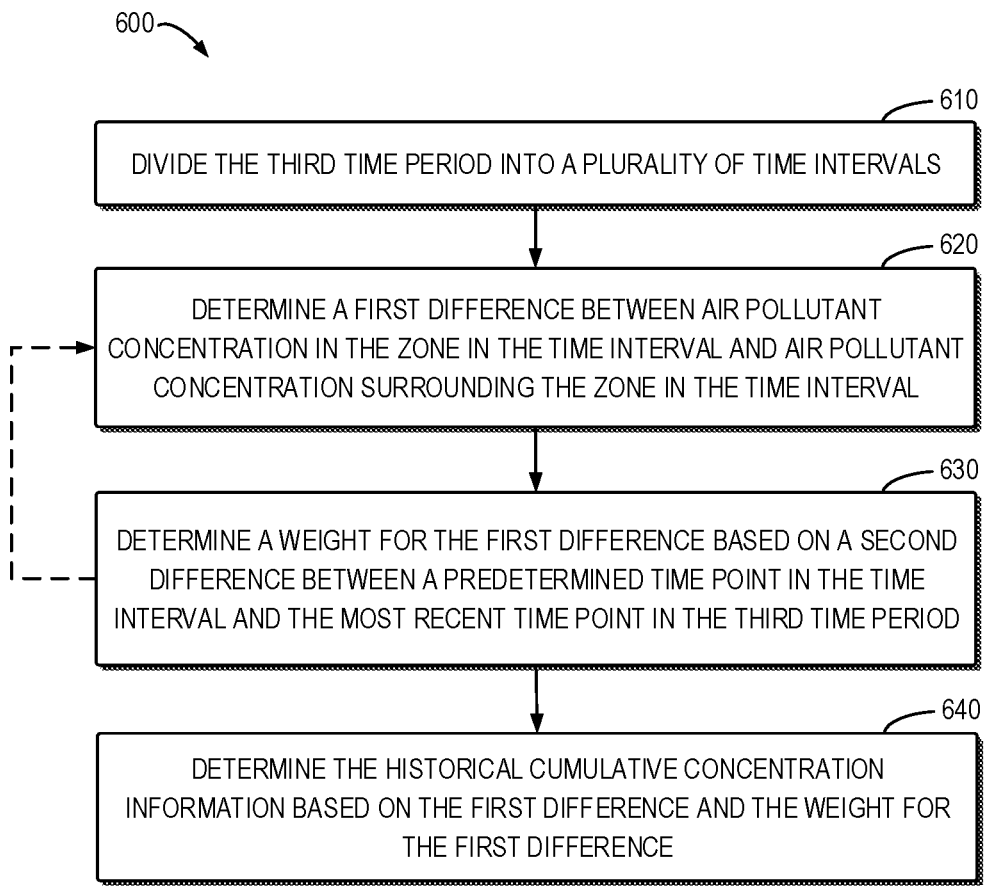
FIG. 6 shows a flow chart of an example method for obtaining historical cumulative concentration information according to an embodiment of the present invention.

A detailed example for obtaining the historical cumulative concentration information is further described with respect to FIGS. 5 and 6, in which FIG. 5 shows an example third time period 500 and FIG. 6 shows a flow chart of an example method 600 for obtaining the historical cumulative concentration information. In obtaining the historical cumulative concentration information, the computer system/server 12 may divide the third time period 500 into a plurality of time intervals, such as the time intervals 510-530 shown in FIG. 5, at 610. For example, the computer system/server 12 may divide the past 24 hours into 24 time intervals, each of which is 1 hour. In this way, the air pollutant concentration accumulated in each time interval can be considered individually.

For each of the plurality of time intervals, the computer system/server 12 may determine a difference (referred to as "concentration difference") between air pollutant concentration in the zone in a respective time interval and air pollutant concentration surrounding the zone in that time interval, at 620. For example, for the time interval 510, the computer system/server 12 may determine a concentration difference between air pollutant concentration in the zone and air pollutant concentration surrounding the zone in the time interval 510.

The concentration difference can indicate whether the air pollutant concentration in the zone is abnormal in comparison with the surroundings. In this case, the computer system/server 12 may also set a threshold for the concentration difference, such that a minor difference can be ignored and an extraordinarily high difference can be capped, thus making the historical cumulative concentration information more accurate.

In addition, for each time interval, the computer system/server 12 may also determine a weight for the concentration difference, at 630. The weight can be determined in various manners. For example, the weight can be determined based on a difference (referred to as "time distance") between a predetermined time point in the time interval and the most recent time point in the third time period. Any time point in the time interval can be selected as the predetermined time point, so as to measure a time distance of the time interval to the most recent time.

For example, the computer system/server 12 may determine the time distance between the time point 511 in the time interval 510 and the most recent time point 501 in the third time period 500, and thus determining the weight for the time interval 510. As another example, the computer system/server 12 may determine the time distance between the time point 521 in the time interval 520 and the most recent time point 501 in the third time period 500, and thus determining the weight for the time interval 520.

The weight decreases as the time distance increases. That is to say, the weight for the time interval 510 is larger than the weight for the time interval 520. As such, the recent air pollutant concentration contributes more to the historical cumulative concentration information, and thus making the historical cumulative concentration information more accurate.

Then, the computer system/server 12 may determine the historical cumulative concentration information based on the concentration difference and the weight for the concentration difference, at 640. Specifically, the computer system/server 12 may determine the historical cumulative concentration information based on the following equations:

$$C = \sum_{t=1}^{i} \phi(t)\min(f(N(t) - \overline{N}(t)), H), \quad (1)$$

$$f(x) = \begin{cases} x & x > k \\ 0 & x \le k \end{cases}, \quad (2)$$

$$\phi(t) = \exp\left(\frac{-t}{100}\right), \quad (3)$$

where C represents the historical cumulative concentration information, t represents the time interval, i represents the number of the time intervals, $\phi(t)$ represents the weight for the respective time interval, N(t) represents the air pollutant concentration in the zone in the respective time interval, $\overline{N}(t)$ represents air pollutant concentration surrounding the zone in the respective time interval, H represents the upper bound threshold for the concentration difference N (t)–$\overline{N}$(t), and k represents the threshold for ignoring the difference between the zone and the surroundings, where setting the concentration difference N (t)–$\overline{N}$(t) below k to 0 means a minor difference between the zone and the surroundings is ignored.

Alternatively and in addition, the weight can also be determined based on the correlation between the first time period and the time intervals in the third time period. For example, the first time period can be the daytime of tomorrow, while the third time period can be the whole day of today. In this case, since the potential pollution source may exhibit a periodic emission behavior, the time intervals fall into the daytime can be thought as more related to the first time period. Thus, the weight for the time intervals falling into the daytime can be set to be higher than that of the other time intervals.

Returning back to FIG. 4, as discussed above, the target area for abnormal air pollution emission prediction is divided into a plurality of zones. In order to reduce the number of zones to be processed, the computer system/server 12 may only obtain the first set of features for a zone including a potential pollution source. In this way, a zone which does not include a potential pollution source and does not emit air pollutant, such as a zone of a river, a mountain, a green space and residential building, can be excluded from the zones to be processed.

To determine whether a zone candidate includes a potential pollution source, the computer system/server 12 may obtain another set of features (referred to as "third set of features") characterizing air condition in a zone candidate. In some embodiments, the computer system/server 12 may obtain the third set of features from the system memory 28. Alternatively, the computer system/server 12 may obtain the third set of features from any storage or database storing the third set of features.

The third set of features is different from the first and second sets of features, and may be point of interest (POI) information and geographic information. Specifically, the third set of features may be an area ratio occupied by a non-pollution source in the zone candidate, a type of the potential pollution source, a size of the potential pollution source, a density of the potential pollution source, a predetermined air pollutant emission scale of the potential pollution source, or time since the zone candidate was last determined to be subject to abnormal air pollution emission.

Then, the computer system/server 12 may determine, based on the third set of features, whether the zone candidate includes a potential pollution source. For example, the computer system/server 12 may compare one or more features with one or more predetermined thresholds, and determine that the zone candidate includes the potential pollution source when the one or more features exceeds the one or more predetermined thresholds. For example, if area ratio occupied by a non-pollution source, such as rivers, mountains, green spaces and residential buildings, in the zone candidate exceeds 60%, it can be determined that the zone candidate does not include a potential pollution source. Alternatively, if the size of the potential pollution source exceeds a medium size, it can be determined that the zone candidate includes a potential pollution source.

After determining that the zone candidate includes a potential pollution source, the computer system/server 12 may determine that this zone candidate is to be further processed, and obtain the first set of features for this zone candidate. In this way, the number of zones to be processed can be reduced, and thus improving the efficiency in the abnormal air pollution emission prediction.

With the obtained first set of features for the zone, the computer system/server 12 determines, based on the first set of features and using a first prediction classifier, whether the zone is subject to abnormal air pollution emission in a future first time period such as tomorrow, at 420. The first prediction classifier can use, for example, the logistic regression or neural network, which can be trained to predict whether the zone is subject to abnormal air pollution emission in the first time period using the first set of features.

In some embodiments, the computer system/server 12 may determine, based on the first set of features and using the first prediction classifier, likelihood (referred to "first likelihood") that the zone is subject to abnormal air pollution emission in the first time period. For example, the computer system/server 12 may compare the first likelihood with a predetermined threshold (referred to as "first predetermined threshold"). If the first likelihood exceeds the first predetermined threshold, the computer system/server 12 may determine that the zone is subject to abnormal air pollution emission in the first time period.

For instance, for a plurality of zones including a potential pollution source, the likelihood of the plurality of zones being subject to abnormal air pollution emission tomorrow can be determined. The computer system/server 12 may rank the likelihood of the plurality of zones, and determine that the zone with rank higher than a predetermined threshold will be subject to abnormal air pollution emission tomorrow. For example, the zone ranked top 10 may be determined to be subject to abnormal air pollution emission tomorrow.

For the zone that is determined to be subject to abnormal air pollution emission in the first time period, it can be further determined a more specific time period in first time period during which the abnormal air pollution will be emitted, thereby increasing the accuracy of prediction. In this case, the computer system/server 12 obtains a second set of features characterizing air condition in the zone, at 430. In some embodiments, the second set of features can be obtained from the system memory 28. Alternatively, the second set of features can be obtained from any storage or database that is able to store the second set of features.

The second set of features is different from the first and third sets of features. The second set of features is related to a second time period, and may be, for example, a number of times the zone being previously determined to be subject to abnormal air pollution emission in the second time period, historical air pollutant concentration in the zone in the second time period, and historical air pollutant concentration surrounding the zone in the second time period.

For example, the second set of features may be the number of times the zone being previously determined to be subject to abnormal air pollution emission in 1 am-2 am in each day of the last week, the historical air pollutant concentration in the zone in 1 am-2 am in each day of the last week, and the historical air pollutant concentration surrounding the zone in 1 am-2 am in each day of the last week. In this way, the historical information about the abnormal air pollution emission condition for a specific time period can be used to predict the abnormal air pollution emission for that specific time period of a future time, such as 1 am-2 am of tomorrow.

At 440, the computer system/server 12 determines, based on the second set of features and using a second prediction classifier, a future second time period in which the zone is subject to abnormal air pollution emission. The second time period is included in the first time period. For example, the first time period may be tomorrow, and the second time period may be the time period of 1 am-2 am of tomorrow. In some embodiments, the second prediction classifier can use the logistic regression or neural network with softmax, which can be trained to predict second time period in which the abnormal air pollution emission will be occurred in the zone.

In some embodiments, the computer system/server 12 may determine, based on the second set of features and using the second prediction classifier, likelihood (referred to as "second likelihood") that the zone is subject to abnormal air pollution emission in the second time period candidate. For example, the computer system/server 12 may determine the likelihood that the zone is subject to abnormal air pollution emission in the time interval of 1 am-2 am of tomorrow.

Then, the computer system/server 12 may compare the second likelihood with a second predetermined threshold. When the second likelihood exceeds the second predetermined threshold, the computer system/server 12 may determine that the second time period candidate to be the second time period.

For example, for a plurality of second time period candidates, the computer system/server 12 may determine the likelihood of the zone being subject to abnormal air pollution emission in these second time period candidates. The computer system/server 12 may rank the likelihood for these candidates, and determine that the second time period candidate with rank higher than a predetermined threshold is the time period during which the zone will be subject to abnormal air pollution emission. For example, it can be determined that the zone is most likely to be subject to abnormal air pollution emission in the time period of 1 am-2 am tomorrow.

In this way, by considering various features affecting and/or representing abnormal air pollution emission in a particular zone, and by first predicting whether the zone will be subject to abnormal air pollution emission in a future first time period, and then predicting a more specific second time period in the first time period that the zone is most likely to be subject to abnormal air pollution emission, the zone with a high level of abnormal air pollution emission can be predicted accurately in time, and the time and resource cost in dealing with the abnormal air pollution emission prediction can be reduced.

FIG. 7 shows a schematic diagram of an example abnormal air pollution emission prediction result 700 according to an embodiment of the present invention. As shown in FIG. 7, abnormal air pollution emission prediction according to an embodiment of the present invention is very precise, and thus facilitating dealing with the abnormal air pollution emission issues efficiently.

It should be noted that the processing of abnormal air pollution emission prediction according to embodiments of this disclosure could be implemented by computer system/server 12 of FIG. 1.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for abnormal air pollution emission prediction using prediction classifiers based on trained neural networks, comprising:
    processing each zone of a plurality of zones based on a first set of features and a first time period by:
        obtaining the first set of features, the first set of features characterizing air condition in a respective zone; and
        predicting, based on the first set of features and using a first prediction classifier of the prediction classifiers, whether the respective zone is subject to abnormal air pollution emission in the first time period;
    upon predicting a zone of the plurality of zones to be subject to the abnormal air pollution emission in the first time period, processing the zone based on a second set of features and a subset of the first time period by:
        obtaining the second set of features, the second set of features characterizing air condition in the zone, wherein the second set of features is different than the first set of features and includes a number of times the zone was previously subject to the abnormal air pollution; and
        predicting, based on the second set of features and using a second prediction classifier of the prediction classifiers, the subset of the first time period and in which the zone is subject to the abnormal air pollution emission; and outputting an indication of at least one of the zone or the subset of the first time period, wherein the indication causes an air pollution emission of the zone to be reduced back to within normal limits;

wherein the processing based on the second set of features is performed only on any zone predicted to be subject to the abnormal air pollution emission in the first time period, wherein the subset of the first time period is shorter in duration than the first time period, and wherein each of the first and second prediction classifiers is based on a respective one of the trained neural networks.

2. The method of claim 1, wherein the subset of the first time period consists of a second time period that is shorter in duration than the first time period, and wherein obtaining the first set of features comprises obtaining at least one of:
  historical cumulative concentration information characterizing air pollutant concentration accumulated in the zone in a third time period that has passed, the zone being the predicted zone;
  historical wind speed in the zone in the third time period;
  historical wind direction in the zone in the third time period;
  historical temperature in the zone in the third time period;
  a number of times the zone being previously predicted to be subject to the abnormal air pollution emission in a fourth time period that has passed;
  whether the zone was predicted to be subject to the abnormal air pollution emission in a fifth time period that has passed; or
  time since the zone was last predicted to be subject to the abnormal air pollution emission.

3. The method of claim 2, wherein obtaining the historical cumulative concentration information comprises:
  dividing the third time period into a plurality of time intervals;
  for each time interval of the plurality of time intervals,
    determining a concentration difference between a first measure of air pollutant concentration in the zone in a respective time interval and a second measure of air pollutant concentration surrounding the zone in the respective time interval;
    determining a weight for the concentration difference based on a time distance between a predetermined time point in the respective time interval and a most recent time point in the third time period, the weight decreasing as the time distance increases; and
  determining the historical cumulative concentration information based on the concentration difference and the weight for the concentration difference.

4. The method of claim 1, further comprising, prior to obtaining the first set of features:
  obtaining a third set of features characterizing air condition in a zone candidate;
  determining, based on the third set of features, whether the zone candidate includes a potential pollution source;
  in response to determining the zone candidate includes the potential pollution source, selecting the zone candidate as the zone rather than as being merely a candidate; and
  obtaining the first set of features for the zone;
  wherein the first, second, and third sets of features each includes a respective, distinct feature.

5. The method of claim 4, wherein obtaining the third set of features comprises obtaining at least one of:
  an area ratio occupied by a non-pollution source in the zone candidate;
  a type of the potential pollution source;
  a size of the potential pollution source;
  a density of the potential pollution source;
  a predetermined air pollutant emission scale of the potential pollution source; or
  time since the zone candidate was last predicted to be subject to the abnormal air pollution emission.

6. The method of claim 1, wherein predicting whether the zone is subject to the abnormal air pollution emission in the first time period comprises:
  determining, based on the first set of features and using the first prediction classifier, a likelihood of the zone being subject to the abnormal air pollution emission in the first time period;
  comparing the likelihood, of the zone being subject to the abnormal air pollution emission in the first time period, with a first threshold likelihood of the zone being subject to the abnormal air pollution emission; and
  in response to determining the likelihood exceeds the first threshold likelihood, predicting the zone is subject to the abnormal air pollution emission in the first time period.

7. The method of claim 1, wherein the subset of the first time period consists of a second time period that is shorter in duration than the first time period, and wherein obtaining the second set of features comprises obtaining at least one of:
  a number of times the zone being previously predicted to be subject to the abnormal air pollution emission in the second time period;
  historical air pollutant concentration in the zone in the second time period; or
  historical air pollutant concentration surrounding the zone in the second time period.

8. The method of claim 1, wherein predicting the subset of the first time period comprises:
  determining, based on the second set of features and using the second prediction classifier, a likelihood of the zone being subject to the abnormal air pollution emission in a candidate time period within the first time period;
  comparing the likelihood, of the zone being subject to the abnormal air pollution emission in a candidate time period within the first time period, with a second threshold likelihood of the zone being subject to the abnormal air pollution emission; and
  in response to determining the likelihood exceeds the second threshold likelihood, determining the candidate time period to be the subset of the first time period.

9. The method of claim 1, wherein the subset of the first time period consists of a second time period that is shorter in duration than the first time period, wherein the zone comprises a first zone of the plurality of zones, and wherein processing of a second zone, different than the first zone, of the plurality of zones based on the second set of features is avoided after the second zone is processed based on the first set of features;
  wherein to improve processing efficiency in performing the air pollution emission prediction, the processing based on the first set of features is performed only on zones determined to be pollution candidates, and the processing based on the second set of features is performed only on the zones predicted to be subject to the abnormal air pollution emission;

wherein the indication comprises an indication of both the zone and the subset of the first time period, wherein the indication causes the air pollution emission of the zone to be reduced back to within the normal limits;

wherein the zone being a pollution candidate is determined based on at least one of (i) an area ratio of pollution-source candidates in the zone to pollution-source non-candidates in the zone exceeding a threshold ratio and (ii) a size of a pollution-source candidate in the zone exceeding a threshold size.

10. A device for abnormal air pollution emission prediction using prediction classifiers based on trained neural networks, comprising:
a processing unit; and
a memory coupled to the processing unit and storing instructions thereon, the instructions, when executed by the processing unit, performing acts including:
processing each zone of a plurality of zones based on a first set of features and a first time period by:
obtaining the first set of features, the first set of features characterizing air condition in a respective zone; and
predicting, based on the first set of features and using a first prediction classifier of the prediction classifiers, whether the respective zone is subject to abnormal air pollution emission in the first time period;
upon predicting a zone of the plurality of zones to be subject to the abnormal air pollution emission in the first time period, processing the zone based on a second set of features and a subset of the first time period by:
obtaining the second set of features, the second set of features characterizing air condition in the zone, wherein the second set of features is different than the first set of features, and includes a number of times the zone was previously subject to the abnormal air pollution; and
predicting, based on the second set of features and using a second prediction classifier of the prediction classifiers, the subset of the first time period and in which the zone is subject to the abnormal air pollution emission; and
outputting an indication of at least one of the zone or the subset of the first time period, wherein the indication causes an air pollution emission of the zone to be reduced back to within normal limits;
wherein the processing based on the second set of features is performed only on any zone predicted to be subject to the abnormal air pollution emission in the first time period, wherein the subset of the first time period is shorter in duration than the first time period, and wherein each of the first and second prediction classifiers is based on a respective one of the trained neural networks.

11. The device of claim 10, wherein the subset of the first time period consists of a second time period that is shorter in duration than the first time period, and wherein obtaining the first set of features comprises obtaining at least one of:
historical cumulative concentration information characterizing air pollutant concentration accumulated in the zone in a third time period that has passed, the zone being the predicted zone;
historical wind speed in the zone in the third time period;
historical wind direction in the zone in the third time period;
historical temperature in the zone in the third time period;
a number of times the zone being previously predicted to be subject to the abnormal air pollution emission in a fourth time period that has passed;
whether the zone was predicted to be subject to the abnormal air pollution emission in a fifth time period that has passed; or time since the zone was last predicted to be subject to the abnormal air pollution emission.

12. The device of claim 11, wherein obtaining the historical cumulative concentration information comprises:
dividing the third time period into a plurality of time intervals;
for each time interval of the plurality of time intervals,
determining a concentration difference between a first measure of air pollutant concentration in the zone in a respective time interval and a second measure of air pollutant concentration surrounding the zone in the respective time interval;
determining a weight for the concentration difference based on a time distance between a predetermined time point in the respective time interval and a most recent time point in the third time period, the weight decreasing as the time distance increases; and
determining the historical cumulative concentration information based on the concentration difference and the weight for the concentration difference.

13. The device of claim 10, further comprising, prior to obtaining the first set of features:
obtaining a third set of features characterizing air condition in a zone candidate;
determining, based on the third set of features, whether the zone candidate includes a potential pollution source;
in response to determining the zone candidate includes the potential pollution source, selecting the zone candidate as being the zone rather than as being merely a candidate; and
obtaining the first set of features for the zone;
wherein the first, second, and third sets of features each includes a respective, distinct feature.

14. The device of claim 13, wherein obtaining the third set of features comprises obtaining at least one of:
an area ratio occupied by a non-pollution source in the zone candidate;
a type of the potential pollution source;
a size of the potential pollution source;
a density of the potential pollution source;
a predetermined air pollutant emission scale of the potential pollution source; or
time since the zone candidate was last determined to be subject to the abnormal air pollution emission.

15. The device of claim 10, wherein predicting whether the zone is subject to the abnormal air pollution emission in the first time period comprises:
determining, based on the first set of features and using the first prediction classifier, a likelihood of the zone being subject to the abnormal air pollution emission in the first time period;
comparing the likelihood, of the zone being subject to the abnormal air pollution emission in the first time period, with a first threshold likelihood of the zone being subject to the abnormal air pollution emission; and
in response to determining the likelihood exceeds the first threshold likelihood, determining the zone is subject to the abnormal air pollution emission in the first time period.

16. The device of claim 10, wherein the subset of the first time period consists of a second time period that is shorter in duration than the first time period, and wherein obtaining the second set of features comprises obtaining at least one of:

a number of times the zone being previously predicted to be subject to the abnormal air pollution emission in the second time period;

historical air pollutant concentration in the zone in the second time period; or historical air pollutant concentration surrounding the zone in the second time period.

17. The device of claim 10, wherein predicting the subset of the first time period comprises:

determining, based on the second set of features and using the second prediction classifier, a likelihood of the zone being subject to the abnormal air pollution emission in a candidate time period within the first time period;

comparing the likelihood, of the zone being subject to the abnormal air pollution emission in a candidate time period within the first time period, with a second threshold likelihood of the zone being subject to the abnormal air pollution emission; and in response to determining the likelihood exceeds the second threshold likelihood, determining the candidate time period to be the subset of the first time period.

18. A computer program product being tangibly stored on a non-transient machine-readable medium and comprising machine-executable instructions, the instructions, when executed on a device, causing the device to perform an operation for abnormal air pollution emission prediction using prediction classifiers based on trained neural networks, the operation comprising:

processing each zone of a plurality of zones based on a first set of features and a first time period by:
obtaining the first set of features, the first set of features characterizing air condition in a respective zone; and
predicting, based on the first set of features and using a first prediction classifier of the prediction classifiers, whether the respective zone is subject to abnormal air pollution emission in the first time period;

upon predicting a zone of the plurality of zones to be subject to the abnormal air pollution emission in the first time period, processing the zone based on a second set of features and a subset of the first time period by:
obtaining the second set of features, the second set of features characterizing air condition in the zone, wherein the second set of features is different than the first set of features and includes a number of times the zone was previously subject to the abnormal air pollution; and
predicting, based on the second set of features and using a second prediction classifier of the prediction classifiers, the subset of the first time period and in which the zone is subject to the abnormal air pollution emission; and outputting an indication of at least one of the zone or the subset of the first time period, wherein the indication causes an air pollution emission of the zone to be reduced back to within normal limits;

wherein the processing based on the second set of features is performed only on any zone predicted to be subject to the abnormal air pollution emission in the first time period, wherein the subset of the first time period is shorter in duration than the first time period, and wherein each of the first and second prediction classifiers is based on a respective one of the trained neural networks.

19. The computer program product of claim 18, wherein the subset of the first time period consists of a second time period that is shorter in duration than the first time period, and wherein obtaining the first set of features comprises obtaining at least one of:

historical cumulative concentration information characterizing air pollutant concentration accumulated in the zone in a third time period that has passed, the zone being the predicted zone;

historical wind speed in the zone in the third time period;

historical wind direction in the zone in the third time period;

historical temperature in the zone in the third time period;

a number of times the zone being previously predicted to be subject to the abnormal air pollution emission in a fourth time period that has passed;

whether the zone was predicted to be subject to the abnormal air pollution emission in a fifth time period that has passed; or time since the zone was last predicted to be subject to the abnormal air pollution emission.

20. The computer program product of claim 18, the operation further comprising, prior to obtaining the first set of features:

obtaining a third set of features characterizing air condition in a zone candidate;

determining, based on the third set of features, whether the zone candidate includes a potential pollution source;

in response to determining the zone candidate includes the potential pollution source, selecting the zone candidate as the zone rather than as being merely a candidate; and obtaining the first set of features for the zone;

wherein the first, second, and third sets of features each includes a respective, distinct feature.

* * * * *